United States Patent [19]

Sramek

[11] Patent Number: 4,861,583

[45] Date of Patent: Aug. 29, 1989

[54] HOT CURLING HAIR TREATMENT

[75] Inventor: John A. Sramek, Racine County, Wis.

[73] Assignee: S. C. Johnson & Son, Inc., Racine, Wis.

[21] Appl. No.: 123,452

[22] Filed: Nov. 20, 1987

Related U.S. Application Data

[63] Continuation-in-part of Ser. No. 903,805, Sep. 4, 1986, abandoned.

[51] Int. Cl.$^4$ .................. A61K 7/06; A61K 7/11
[52] U.S. Cl. .................................. 424/70; 424/71; 424/8
[58] Field of Search .............. 424/DIG. 2, 70, 71

[56] References Cited

U.S. PATENT DOCUMENTS

| | | | |
|---|---|---|---|
| 2,309,722 | 2/1943 | Wilkes et al. | 424/70 |
| 2,691,378 | 10/1954 | Oliva | 424/DIG. 2 |
| 2,979,528 | 4/1961 | Lundsted | 548/312 |
| 2,983,650 | 5/1961 | Rubin | 424/DIG. 2 |
| 3,130,127 | 4/1964 | Tarpey | 424/DIG. 2 |
| 3,133,865 | 4/1964 | Richardson et al. | 424/71 |
| 3,188,275 | 6/1965 | Erlemann | 424/DIG. 2 |
| 3,461,073 | 8/1967 | Crowell, Jr. et al. | 424/70 |
| 3,479,427 | 11/1969 | Lieberman et al. | 424/70 |
| 3,482,581 | 12/1969 | Weigand | 424/71 |
| 3,579,465 | 5/1971 | Schmolka | 252/316 |
| 3,634,022 | 2/1972 | Robbins et al. | 424/70 |
| 3,906,091 | 9/1975 | Zviak et al. | 424/70 |
| 3,937,802 | 2/1976 | Fujimoto et al. | 424/47 |
| 3,946,749 | 3/1976 | Papantoniou | 424/DIG. 2 |
| 3,990,459 | 11/1976 | Papantoniou | 424/DIG. 2 |
| 4,048,301 | 9/1977 | Papantoniou | 424/70 |
| 4,115,549 | 9/1978 | Scott | 424/71 |
| 4,165,367 | 8/1979 | Chakrabarti | 424/70 |
| 4,192,862 | 3/1980 | Pengilly | 424/70 |
| 4,283,384 | 8/1981 | Jacquet et al. | 424/70 |
| 4,318,901 | 3/1982 | Ishida et al. | 424/70 |
| 4,376,114 | 3/1983 | Jacquet et al. | 424/47 |
| 4,378,345 | 3/1983 | Okumura et al. | 424/DIG. 2 |
| 4,402,977 | 9/1983 | Grollier et al. | 424/70 |
| 4,452,261 | 6/1984 | Bresak et al. | 132/7 |
| 4,493,824 | 1/1985 | Abe | 424/70 |
| 4,533,545 | 8/1985 | Sebag | 424/70 |
| 4,638,822 | 1/1987 | Grollier et al. | 424/70 |
| 4,753,793 | 6/1988 | Walton | 424/71 |

FOREIGN PATENT DOCUMENTS 50-101540 8/1975 Japan .
60-116624 6/1985 Japan .

OTHER PUBLICATIONS

Chem. Abst. 83:197694x (1975).
Chem. Abst. 104:10369g (1985).
Gaylord, *Polyethers*, pp. 197–200, 213–221, and 231–237 (1963).
*CTFA Cosmetic Ingredient Dictionary*, Estrin et al., Ed., The Cosmetic, Toiletry & Fragrance Assoc., Inc. p. xi, 203, 1982.
PCT International Search Report, Appln. No. PCT/US88/00279, filed 2/1/88, 7 pages (5/18/88).
PCT International Search Report, Appln. No. PCT/US87/02161, filed 8/21/87, 5 pages (12/1/87).
*CTFA Cosmetic Ingredient Dictionary*, 34d Ed., The Cosmetic, Toiletry & Fragrance Assoc., Inc., Wash. D.C., 1982, pp. 246, 257, 508.
"Jheri Redding ® Thermal Styling Lotion," Jheri Redding Products, Dist., Div. of Conair Corp., Edison, NJ, label.
"By-Degrees TM Heat Styling Lotion with Thermistor Action", Fermodyl Div. of Syntex Beauty Care, Inc., Los Angeles, CA, label.

*Primary Examiner*—Douglas W. Robinson
*Assistant Examiner*—Richard Kearse

[57] ABSTRACT

A heat activated hair curling treatment composition containing an effective amount of a certain linear or branched or crosslinked water soluble polyethylene oxide polymer having a melting point of 50° to 80° C. and a molecular weight in a range of from 50,000 to 250,000 for the linear polymers and from about 20,000 to 250,000 for the branched or crosslinked polymers. The composition may be formulated into aerosols or pump sprays and facilitates long lasting hair styling without damaging hair. The polymer is exposed to heat from a curling iron which causes it to melt thereby imparting a curl to the hair. The composition is comprised of the polyethylene oxide polymer, optionally, at least one surfactant, and a cosmetically acceptable solvent such as water, ethanol and mixtures thereof.

10 Claims, No Drawings

HOT CURLING HAIR TREATMENT

This application is a continuation-in-part of U.S. Ser. No. 06/903,805, filed on Sept. 4, 1986 now abandoned.

BACKGROUND OF THE INVENTION

1. Field of the Invention

This invention relates to a heat activated hair treating composition and more particularly, a heat activated hair treating composition which contains as an effective component a branched or cross-linked polyethylene oxide polymer having a melting point of about 50° to 80° C. and an average molecular weight in the range of greater than or equal to 20,000 or a linear polyethylene oxide polymer having a molecular weight in the range of greater than or equal to about 50,000 and to a method of treating the hair with such compositions. The heat activated hair treating composition may be formulated into aerosols, gels, lotions or pump sprays and facilitates long lasting hair styling without damaging hair and without need to resort to expensive salon treatments.

2. Description of the Prior Art

Hair treating compositions are old and well known in the art. It has been particularly sought after by those skilled in the art to provide a composition which allows for home treatment to style the hair without resulting in damage to the hair. The compositions should also be water soluble and easily rinsed from the hair when desired.

Okumura et al., U.S. Pat. No. 4,378,345 discloses a hair setting composition which has a polyethylene glycol with an average molecular weight of 6,000 to 30,000. The composition further includes a hair setting composition which has as effective components a polyethylene glycol having an average molecular weight of 6,000 to 30,000 and a divalent or trivalent metal salt of pyrrolidone carboxylic acid and/or polyoxyalkylene-added silicone oil. These hair setting compositions are formulated into various aerosols, lotions or pump spray types to facilitate a long lasting shine on the hair. The polyethylene glycol is present in the range of about 0.05 to 5% by weight of the composition. The divalent or trivalent metal salt of the pyrrolidonecarboxylic acid is present in an amount of 0.01 to 3% by weight of the composition. Finally, when present, the polyoxyalkylene-added silicone oil is present in an amount of about 0.1 to 5% by weight of the composition.

The present invention differs from Okumura in that Okumura is directed to a straight chain polyethylene glycol (i.e., oxide) polymer composition wherein the present invention is directed to straight chain (i.e., linear) polyethylene oxide having a higher average molecular weight (i.e., at least 50,000) or a branched or cross-linked polyethylene oxide polymer for the purpose of imparting hold to the hair. Furthermore, Okumura does not disclose curling the hair with a heated curling iron. Moreover, the present invention does not envision the use of divalent or trivalent metal salts of pyrrolidonecarboxylic acid and neither is there any contemplation for the use of a silicone containing product. Accordingly, the present invention differs from Okumura.

Wilkes et al., U.S. Pat. No. 2,309,722 relates to a toilet preparation containing polyalkylene glycols. The toilet preparations are hair preparations which are used to impart a wave or permanent to the hair. The polyethylene glycols useful are those having a molecular weight of not less than about 400 and have a molecular average weight of anywhere from 400 to 4,000.

Wilkes differs from the present invention in that Wilkes is directed to a relatively low molecular weight straight chain polyethylene glycol polymer whereas the present invention requires higher average molecular weight linear or branched or cross-linked polyethylene oxide polymers. Further, Wilkes discloses that a polyethylene glycol having a molecular weight of above about 4,000 tend to become waxy and flake off unless plasticized with a suitably compatible water soluble material. Finally, Wilkes does not disclose the use of a curling iron to apply heat to the hair to activate the polyethylene glycol. Accordingly, the present invention differs from Wilkes.

Oliva, U.S. Pat. No. 2,691,378 discloses a permanent wave lotion having as active ingredients a proteinaceous material such as casein, and a polyalkylene glycol having 400 and preferably 1,000 recurring ethyleneoxy groups in a molecule which is a polyethylene glycol although the polymers employed can further contain up to 4,000 to 6,000 recurring ethylenoxy groups. Oliva further teaches that approximately equivalent results can be obtained using polyalkylene glycol polymers containing the same number of recurring propyleneoxy or butyleneoxy groups. The lotion must be an aqueous alkaline medium which is said to attack the cystine of the hair and disrupt the disulfide bonds therein. The lotion is applied to the hair and inter alia, the hair is curled with curlers or a curling rod and heated to produce a curl or wave. However, heating is not required, although it is said to speed the action of the lotion. The curl or wave is permanent and will not wash out with shampooing.

In Oliva, the solution is applied to the hair and is, optionally, heated. The hair is then rinsed with an acid solution or acid bath to set the lotion and then the hair is rinsed of the acid. The resulting wave cannot be washed out of the hair by water.

The present invention differs from Oliva in that the present invention is a relatively high molecular weight linear or a branched or cross-linked polyethylene oxide polymer which is water soluble, which does not require an acid bath to fix it in place, and which can be rinsed from the hair by regular shampooing. The pH of the compositions of the present invention can be acidic or basic while Oliva requires an alkaline medium in addition to a proteinaceous material. Accordingly, the present invention differs from Oliva.

Erlemann, U.S. Pat. No. 3,188,275 discloses a hair setting preparation for use on towel dried or dampened hair which consists of a vinyl acetate polyethylene glycol copolymer in a range of about 1 to 10%, and panthenol or panthenol ether. The copolymer of Erlemann requires vinyl acetate as a comonomer while the present invention does not employ such copolymers. Accordingly, the present invention differs from Erlemann.

Lieberman et al., U.S. Pat. No. 3,479,427 discloses a hydrated dialdehyde starch having a dialdehyde number of at least 50 and a cosmetically acceptable vehicle. This patent is of interest because it discloses as a non-active ingredient a plasticizer for the dialdehyde which may be a polyethylene glycol material. There is no disclosure of the use of a linear high molecular weight polyethyleneoxide polymer of greater than about 50,000 or a cross-linked or branched polyethyleneoxide glycol polymer as the active ingredient in imparting a temporary set to the hair. Accordingly, the present invention differs from Lieberman, et al.

Papantoniou, U.S. Pat. No. 3,946,749 discloses a cosmetic composition which comprises at least one graft and cross-linked copolymer obtained by copolymerization of at least one nonionic monomer, at least one ionic monomer of N-vinyl pyrrolidone, polyethylene glycol and a cross-linking agent. These compositions are useful as hair lacquers and wave setting lotions and adhere well to the hair. Papantoniou differs from the present invention in that there is no teaching of the application of heat to melt the polymer to give the hair setting qualities. The cross-linking and grafting of the copolymer of Papantoniou differs from the present invention in that the present invention does not include a nonionic monomer or an anionic monomer. Finally, the melting temperature of the Papantoniou polymer is not within the ranges contemplated in the present invention. Accordingly, the present invention differs from Papantoniou. U.S. Pat. No. 3,990,459 to Papantoniou teaches cationic graft and cross-linked copolymers in wavesetting lotions and is similar in disclosure to the Papantoniou '749 patent although the polymers employed are different. In both, the polyethyleneoxide polymer is grafted into the copolymer whereas the present invention employs polyethyleneoxide polymers with only a minor proportion of a polypropylene glycol.

SUMMARY OF THE INVENTION

The present invention is a leave-on, heat activated hair treatment containing certain polyethylene oxide polymers as a major component which causes the hair to have an excellent heat set. The polyethylene oxide polymers are water soluble linear polymers which have an average molecular weight between about 50,000 and 250,000, more preferably between about 80,000 and 150,000, or a water soluble branched or crosslinked polyethylene oxide polymer having an average molecular weight of at least 20,000 up to about 250,000, and more preferably, from 20,000 to 100,000. The preferred polymers are the branched or crosslinked polymers because they tend to form clear solutions in water, have less waxy character than the linear polymers and have greater substantivity to the hair. The polymer has a melting point in the range of about 50° to 80° C. The polymer forms a strong film upon cooling that is moisture resistant but is easily shampooed out of the hair.

The hair is treated according to a method whereby at least 1% polymer solution is applied to the hair in any convenient form. The hair is first washed to remove any excess oils or dirt and then at least a 1% polymer solution in water is added and worked throughout the hair. The hair is then dried and curled with a hot curling iron. The hair takes on the curl which has a natural feel to it and is not sticky or hard to the touch and yet will not damage the hair. The polymer can then be washed out of the hair at any time to allow for changes in style. Other components of the composition include gelling polymers, surfactants, wetting agents, dyes, perfumes, anti-static agents and conditioning agents such as fatty quaternary ammonium compounds or amine salts.

DETAILED DESCRIPTION OF THE PREFERRED EMBODIMENT

The present invention is a heat activated hair treating composition which comprises a water soluble higher average molecular weight linear or a branched or crosslinked polyethylene oxide polymer, optionally at least one surfactant, and a cosmetically acceptable solvent. The term "heat activated" is intended to mean that the polymer has a relatively sharp melting point in a range provided by a hair curling iron so that the polymer quickly reverts to its solid state upon removal of heat and retains the hair tress in its curled state. The term "water soluble" is intended to mean that the polymer has a "Cloud Point" in 1% by weight aqueous solution that is above 30° C. (i.e., a 1% solution of the polymer forms a clear solution in water until the Cloud Point temperature is reached at which time the solution becomes hazy or cloudy).

The water soluble polyethylene oxide polymer is present in an amount of about 0.1 to 20% by weight of the composition and is preferably present at 3% of the composition. The linear polyethylene glycol polymers can be made by the reaction of ethylene oxide in the presence of a catalyst such as a base according to well known techniques. As described below, a minor amount of propylene oxide can also be included in the polyethylene oxide polymers useful in the present invention.

The branched or crosslinked polymer may be formed from the reaction of an initiator which is a polyhydric organic compound containing 3 or more reactive alcoholic hydrogen groups and/or amine hydrogen groups selected from the group consisting of erythritol, pentaerythritol, sorbitol, triethanolamine, ethylenediamine, 2-amino,2-methyl-propanol, 2-amino,2-methyl-propanediol, ammonia, and mixtures thereof, or an initiator having 2 or more epoxy groups such as erythritol anhydride, with a base such as sodium hydroxide, and ethylene oxide, or optionally, but additionally in relatively minor proportions, propylene oxide. Instead of ethylene oxide and propylene oxide, it is understood that polyethylene oxide, polypropylene oxide or copolymers of both can be added to the initiator.

It should be understood that propylene oxide should be no more than about 40 percent of the total moles of ethylene oxide and propylene oxide employed since propylene oxide tends to reduce the water solubility of the resulting polymer and lowers the melting point below 50° C. Preferably, no propylene oxide is included in the polymers for optimum water solubility. The resulting polymer should be capable of forming a moisture resistant solid film at room temperature (20°–25° C.) up to body temperature (37° C.). The linear polymer should have a number average molecular weight between about 50,000 and 250,000, more preferably between about 50,000 and 150,000, and the water soluble branched or crosslinked polyethylene oxide polymer should have a number average molecular weight of at least 20,000 up to about 250,000, and more preferably, from 20,000 to 100,000. More preferred are the branched or crosslinked polymers and while the Examples describe such polymers in the range of 20,000 to 30,000 average molecular weight, it is believed at present that polymers having average molecular weights closer to 100,000 would be more preferred.

The polymer has a melting point in a range of about 50° to 80° C. and preferably from 55° to 65° C. Pure high molecular weight polyethylene oxide polymers generally have a melting point of about 65° C. When subjected to such heat from, for example a hair curling iron, the polymer melts and exhibits excellent substantivity to the keratin in human hair. Upon cooling, it forms a strong moisture resistant film which feels natural to the touch and yet which imparts a set to the hair which does not damage the hair as conventional permanent wave solutions often do.

Linear polyethylene oxide polymers of the above type are well known in the art and a number of such polymers are available from various commercial sources such as from Union Carbide Corporation. Polymers of the above branched and crosslinked type are known in the art as can be seen from an examination of pages 197–200 and 233–237 of *Polyethers, Part I. Polyalkylene Oxides and Other Polyethers*, N. Gaylord, Editor, Interscience Publishers, (1963) and the references to other patents and publications cited therein. Some of such polymers are available from manufacturers such as BASF-Wyandotte Corporation of Parsippany, N.J., Mazer Chemicals, Inc. of Gurnee, IL and Union Carbide Corporation of Danbury, CT For example, certain TETRONIC® brand block copolymer surfactants sold by BASF-Wyandotte Corporation can be used such as TETRONIC 1508 which is reported to be a block copolymer which is the reaction product of ethylene diamine with propylene oxide followed by ethylene oxide having an average molecular weight of about 30,000, a melting point of about 60° C. and a Cloud Point in excess of 100° C. Other examples of TETRONIC® brand polymers which may be useful herein are TETRONIC 908, 909, 1107, 1307, and 150R8 copolymer surfactants. The TETRONIC® brand polyols are reported by the manufacturer to be the subject of U.S. Pat. No. 2,979,528.

The polymer is carried in a solvent of the type commonly used in hair fixative compositions such as those selected from the group consisting of water, aliphatic alcohols having from 2 to 4 carbon atoms such as ethanol, isopropanol and n-butanol, glycols such as propylene glycol and mixtures thereof. Preferably, the polymer is carried in a solvent selected from the group consisting of water, ethanol and mixtures thereof. The amounts of these solvents may vary according to how the solution is to be used. For example, ethanol may be used when a hair spray application is envisioned and water when not in a spray form. However, it is preferred to have both solvents present for maximum benefit.

The composition further optionally includes a surfactant which may be a foaming surfactant to add conditioning benefits or dissolve the polymer or other ingredients in the solvent solution. The surfactants, of which one or more may be present, are selected from the group consisting of quaternary surfactants such as stearyl benzyl dimethyl ammonium chloride, cetyl trimethyl ammonium chloride; 3° amine salts such as stearyl amido propyl dimethyl ammonium chloride, acetate, or lactate and stearyl dimethyl ammonium chloride, acetate or lactate; nonionic emulsifiers such as oleoyl alcohol with 10–20 moles of ethoxylation, sorbitol esters of $C_{12}$–$C_{18}$ fatty acids such sorbitan oleate or palmitate and ethoxylated sobitol esters of $C_{12}$–$C_{18}$ fatty acids such as laurate esters of sorbitan condensed with about from 4 to about 20 moles of ethylene oxide, amphoteric surfactants such as fatty acid derivatives of amino acids such as $RCONHCH_2CH_2N^+(CH_2CH_2OH)(CH_2COO^-)CH_2COONa$, $RCONHCH_2CH_2N(CH_2CH_2OCH_2CH_2COONa)CH_2CH_2COONa$, $RCONHCH_2CH_2N(CH_2CH_2OH)CH_2COONa$, $RCONHCH_2CH_2N(CH_2CH_2OH)CH_2CH_2COONa$, betaines such as $RCONH(CH_2)_3N^+(CH_3)_2CH_2COO^-$ and mixtures thereof where RCO— represents either the coconut acid or the lauric acid radical. Surfactants useful in cosmetic preparation are well known in the art. The surfactants are present in an amount of up to 50% by weight of the polymer.

The composition may optionally include conditioners and anti-static ingredients such as those described above as being quaternary surfactants and tertiary amine salts, all present in an amount of up to about 50% by weight of the polymer weight.

The solution may also be made into a gel in which case a carbomer thickening agent (i.e., a polymer of acrylic acid crosslinked with a polyfunctional agent such as a polyallyl ether of sucrose) such as Carbopol 941 available from B. F. Goodrich could be used. The thickener is present in an amount of about 0.5 to 3%, typically 1% by weight of the composition. Those skilled in the art will appreciate that any cosmetically acceptable thickening agent will prove useful for this purpose, in the amounts indicated herein.

In whatever form the composition takes, the pH is in a range of from about 3 to 9 when the composition contains at least 50% water or a sufficient amount of water is added to permit the pH of the composition to be measured.

The hair may be treated by first washing the hair to remove any excess oils and dirt, applying the heat activated solution comprising the polymer, optionally one surfactant and solvent, drying the hair and finally applying a heat source such as a curling iron which radiates heat in the range of about 60° to 180° C. and preferably 80° to 150° C. The polymer then melts and forms a moisture resistant film over the hair which gives the hair a good memory and imparts a curl to the hair which does not damage the tertiary structure of the hair and is easily washed out of the hair to allow for changes of style. The composition may be incorporated into mousses, gels, hair sprays, lotions or any leave on products.

The following examples are offered to show various forms and formulations. They are intended to be as illustrative and not as limiting to the scope and spirit of the invention.

In the following Examples, the ingredients used were as follows and the amounts thereof are in parts by weight unless otherwise indicated:

Cetrimonium Chloride is cetyl trimethyl ammonium chloride (VARIQUAT® E228 from Sherex Chemical Company at 25% active level is one example).

GAFQUAT® 734 is a copolymer of vinylpyrollidone and dimethyl aminoethyl methacrylate quaternized with dimethyl sulfate, available from GAF.

KATHON® CG—5-chloro-2-methyl-4-isothiazolin-3-one preservative from Rohm & Haas Company.

MACOL 215-124 obtained from Mazer Chemicals, Inc. was a polyether hexol having an average molecular weight of about 30,000 which was the reaction product of sorbitol and ethylene oxide having a melting point of 55°–65° C. and a Cloud Point of greater than 100° C.

TETRONIC® 1508 Block Copolymer Surfactant from BASF Wyandotte Corporation is the reaction product of ethylene diamine with a minor amount of propylene oxide followed by reaction with ethylene oxide to obtain a polymer having an average molecular weight of about 30,000 having a Cloud Point of greater than 100° C. and a melting point of about 60° C. The *CTFA Cosmetic Ingredient Dictionary*, Third Edition, 1982, reports that this polymer is Poloxamine 1508 having the structure $H(OCH_2CH_2)_y(OCH_2CH(CH_3))_xNCH_2CH_2N-(CH(CH_3)C-$ $H_2O)_x(CH_2CH_2O)_yH$ where the values of x and y are respectively 22 and 122.

U.C. CARBOWAX® 3350 from Union Carbide corresponds to the structure $H(OCH_2CH_2)_nOH$ having an average molecular weight of 3,000–3700 and has a melting point of 54° to 58° C.

U.C. CARBOWAX® 20M from Union Carbide corresponds to the structure $H(OCH_2CH_2)_nOH$ where n has an average value of about 350, thus having a molecular weight of about 15,440. The Cloud Point of this polymer was reportedly greater than 100° C. and the softening point was reportedly 50°–55° C.

U.C. MLX 2584 is the tradename of a branched or crosslinked polyethylene oxide polymer having a melting point of about 55° to 65° C. and a molecular weight in the range of greater than or equal to 20,000.

U.C. POLYOX® WSR N10 from Union Carbide corresponds to the structure $H(OCH_2CH_2)_nOH$ where n has an average value of about 2000, thus having a molecular weight of about 88,000. The Cloud Point of this polymer was reportedly greater than 100° C. and the melting point was reportedly 65° C.

U.C. POLYOX® WSR N3000 from Union Carbide corresponds to the structure $H(OCH_2CH_2)_nOH$ where n has an average value of about 14000, thus having a molecular weight of about 616,000. The Cloud Point of this polymer was reportedly greater than 100° C. and the melting point was reportedly 65° C.

In the following Examples, the following test was used to evaluate the performance of the compositions of the present invention on the hair:

Curl Drop Test—a 2 gram tress of virgin brown human hair is treated by washing in hair shampoo and rinsing. The wet swatches are then treated with 1 gram of the composition to be tested, combed through 10 times with a comb, the excess composition is squeezed out by hand, allowed to air dry at room temperature (25° C.) and 50% relative humidity and the treated tress is hot-curled using a conventional, electrically-heated hair-curling iron. The diameter of the curling iron and thus the curl formed was 19 millimeters. One end of the curled tress is suspended from a stand and the length of the curled tress is measured. The tress, mounted on the stand, is then stored at 25° C. and at the relative humidity reported in the Examples for the specific period of time reported in the Examples where the test was run. The length of the tress is again measured and the difference between the initial length and the length after storage is reported as "Curl Drop", i.e., relaxation of the curl in the hair tress.

In the following Examples, the composition was applied to the hair tress and was not rinsed off with water. The tress was wrung to remove excess composition before allowing it to air dry or before hot curling to simulate the manner in which a consumer would use the composition.

EXAMPLE 1

In this Example, some exemplary formulations for pump spray use are given along with ranges for the various ingredients contained therein.

| Example No. Pump Spray Formulas | 1A Reg. Hold | 1B Extra Hold | Ingredient Range |
|---|---|---|---|
| U.C. MLX 2584 | 3.0 | 3.0 | 1–6% |
| Cetrimonium Chloride | 0.25 | 0.25 | 0–3 |
| Ethanol (SDA 40) | 35.0 | 35.0 | 0–50 |
| H₂O | 61.549 | 59.585 | Balance |
| Fragrance | 0.2 | 0.2 | 0–5 |
| Citric acid | 0.001 | 0.0015 | 0–.1 |
| GAFQUAT 734 | — | 2.0 | 0–5 |

The compositions may be prepared by heating the water and U.C. MLX 2584 together with stirring to about 120° F. and continuing stirring until the polymer is dissolved. The solution is then cooled to room temperature and the following ingredients are stirred into the solution in the following order: ethanol, cetrimonium chloride, citric acid (1% solution in water), and fragrance.

The hair is wet at time of application, and styled when dry. There is a significant improvement in hot curling using a curling iron. The formulas result in fuller style, better appearance and enhanced manageability. The product is easily removed with shampooing as desired.

EXAMPLE 2

In Examples 2–3, the branched or cross-linked UC MLX 2584 polymer was tested versus a linear polyethylene oxide polymer. The linear polyethylene oxide polymer employed in comparative Example 4 was Union Carbide CARBOWAX® 20M having an average molecular weight of about 15,440 while the UC MLX 2584 polymer was not linear and had an average molecular weight of between 20,000 and 26,000 according to the manufacturer.

The compositions tested were as follows:

| Example No. | 2 | 3 |
|---|---|---|
| U.C. MLX 2584 | 3.0 | — |
| U.C. CARBOWAX (R) 20 M | — | 3.0 |
| Ethanol | 35.0 | 35.0 |
| H₂O | 62.0 | 62.0 |

Example 2 produced a clear solution which formed a translucent film when allowed to air dry at room temperature on a glass slide. Example 3 produced a slightly hazy solution and a precipitate was observed to form. Example 3 formed a cloudy, opaque film when allowed to air dry on a glass slide.

The Curl Drop Test was performed using each of the above compositions. Two swatches of virgin brown hair, 10 inches in length and weighing 2 grams, from DeMeo Brothers of New York, N.Y. were used for each composition tested in these and in the following Examples. During combing of the wet tress, Example 2 did not foam while Example 3 did foam during combing. Foaming is undesirable because the user may think that the shampoo used to wash the hair has not been rinsed away from the hair.

The tresses treated with Example 2 was observed to be stiff and shiny after air drying while the tresses treated with Example 3 were only observed to be stiff. The tresses treated with Example 2 had a tight curl which is more desirable than the loose curl observed for the treated with Example 3.

After 3 hours at 25° C. and a relative humidity of 50%, the average Curl Drop for the two tresses treated with Example 2 was 9/16 inch while the average Curl Drop for the tresses treated with Example 3 was 1 1/16 inches. Thus, the Curl Drop for tresses treated with Example 3 was ½ inch more than Example 2. After this test was run, the tresses were again recurled with the same electrically heated curling iron and allowed to hang from a stand overnight and the average curl diameter was then measured. The tresses treated with Example 2 had an average diameter of the curl of 35 millimeters while the tresses treated with Example 3 had an average diameter of 41 millimeters indicating that Example 2 retained a tighter curl overnight than did Example 3. Thus, the composition of Example 3 was inferior to that of Example 2 in several ways.

EXAMPLES 4–6

These Examples are similar to those of Examples 2–3 in that the U.C. MLX 2584 polymer (Example 4) was compared to a linear polyethylene oxide polymer having an average molecular weight in the range of 3,000–3,700 (comparative Example 5) and a treatment only using water (comparative Example 6). The formulation used was as follows:

| Example No. | 4 | 5 | 6 |
|---|---|---|---|
| U.C. MLX 2584 | 1.0 | — | — |
| U.C. CARBOWAX (R) 3350 | — | 1.0 | — |
| H₂O | 98.95 | 98.95 | 100.0 |
| KAHON CG | 0.05 | 0.05 | — |

The Curl Drop was measured insert on one tress for each composition at 25° C. and 54% relative humidity. The initial length of each tress and the cumulative increase in length (" denotes inches) with time (i.e., Curl Drop) were as follows:

| | Initial | Curl Drop | | |
|---|---|---|---|---|
| Example | Length | 30 Minutes | 1 Hour | 4 Hours |
| 4 | 6 9/16" | 1/16" | 1/16" | 2/16" |
| 5 | 6 13/16" | 3/16" | 4/16" | 6/16" |
| 6 | 7 4/16" | 12/16" | 15/16" | 22/16" |

Example 4 gave the least amount of Curl Drop. Example 5 was better than the control Example 6 using water, but its performance was inferior to Example 4. Example 5 was also inferior to Example 4 in initial curl length.

EXAMPLES 7–10

In these Examples, the U.C. MLX 2584 was evaluated in compositions of the present invention versus a nitrogen-containing polymer, TETRONIC 1508, and the linear polyethylene oxide polymer U.C. POLYOX WSR-10. The formulations used were as follows:

| Example No. | 7 | 8 | 9 | 10 |
|---|---|---|---|---|
| U.C. MLX 2584 | 2.0 | 2.0 | — | — |
| TETRONIC 1508 | — | — | 2.0 | — |
| U.C. POLYOX WSR-N10 | — | — | — | 1.0 |
| Lactic acid (10%)[1] | — | — | 0.27 | — |
| H₂O | 97.95 | 97.95 | 97.68 | 98.954 |
| KATHON CG | 0.05 | 0.05 | 0.05 | 0.05 |

[1] Ten percent in water.

Example 9 contained lactic acid to reduce the alkalinity of the TETRONIC 1508 polymer. Examples 7 and 8 were duplicate runs to test reproducibility. The pH of Example 9 was found to be 5.4. The results for each Example reported below are for results obtained on a single tress of hair rather than an average of several tresses. Each tress was air dried and then hot curled using an electrically heated curling iron. The results are reported below:

| Ex. No. | Air Dried | Hot Curled |
|---|---|---|
| 7 | Stiff — | Stiff |
| 8 | Stiff — | Stiff |
| 9 | Stiff | Very Stiff |
| 10 | Very Stiff, Good Bounce | Stiff + |

One problem noted in other work with the U.C. POLYOX WSR-N10 polymer was that the solutions tended to be hazy and to contain a precipitate at concentrations of about 1–5% even after addition of a solvent such as ethanol and small amounts (0.1 to 0.4%) of surfactants such as TWEEN 20 OR BRIJ 52 from ICI Americas, Inc. were added. The U.C. MLX 2584 polymer resulted in more desirable clear solutions which did not form precipitates in water solution.

The feeling of the hair tress to the touch was evaluated on a scale of increasing stiffness with Stiff— being the least stiff followed by Stiff, Stiff+ and Very Stiff. Examples 7 and 8 were the least stiff while Example 9 was noted to be Very Stiff after hot curling while Example 10 was Very Stiff when air dried and when hot curled. Example 10 gave a hair tress with good bounce after air drying.

The following reports the Curl Drop of the Examples 7–10. Examples 7–9 were comparable in performance. Example 10 was the best in Curl Drop since it was noted to be rather stiff to the touch. It was also had a rather high molecular weight relative to the other samples tested in this series. The 24 Hour figure given was after the tresses were stored overnight at from 60% to 40% relative humidity (humidity changed overnight).

| | Initial | Curl Drop, 60% R.H. | | | | |
|---|---|---|---|---|---|---|
| Ex. No. | Length | 1 Hr. | 2 Hr. | 6 Hr. | 8 Hr. | 24 Hr. |
| 7 | 6 12/16" | 3/16" | 4/16" | 11/16" | 12/16" | 16/16" |
| 8 | 6 11/16" | 4/16" | 5/16" | 12/16" | 14/16" | 17/16" |
| 9 | 6 11/16" | 6/16" | 8/16" | 14/16" | 14/16" | 17/16" |
| 10 | 6 11/16" | 4/16" | 5/16" | 8/16" | 9/16" | 11/16" |

Each tress used above was then combed 10 times and the initial length after combing was recorded. The Curl Drop after combing was then measured after 3.5 hours and after 24 hours at 40% relative humidity. The results are reported below. All Examples were comparable in performance.

| | Initial | Curl Drop, 60% R.H. | |
|---|---|---|---|
| Ex. No. | Length | 3.5 Hr. | 24 Hr. |
| 7 | 8 0/16" | 4/16" | 6/16" |
| 8 | 7 14/16" | 2/16" | 5/16" |
| 9 | 7 12/16" | 3/16" | 5/16" |
| 10 | 7 7/16" | 3/16" | 6/16" |

EXAMPLES 11–12

In these Examples, the use of MACOL 215-124 in compositions of the present invention was demonstrated versus U.C. MLX 2584. The formulations used were as follows:

| Example No. | 11 | 12 |
|---|---|---|
| MACOL 215-124 | 1.0 | — |
| U.C. MLX 2584 | — | 1.0 |
| H₂O | 98.95 | 98.95 |
| KATHON CG[1] | 0.05 | 0.05 |

[1] One drop was added, about 0.05 grams.

MACOL 215-124 was found to be insoluble in absolute ethanol, but was soluble in 95% ethanol (5% water) at 1.5% solids. Example 11 resulted in a clear solution and Example 12 was slightly hazy. Hair treated with each composition was stiff to the touch after air drying, no powdering was noted when either dry, treated tress was combed and both treated tresses exhibited static when combed. Example 11 gave an air dried tress having a dark brown appearance while Example 12 had a brown appearance, indicating that more of the natural color of the tress was shown by the Example 11 treatment. After hot curling with an electrically heated curling iron, a tress treated with Example 11 took an excellent curl with very good combability and the hair was left dark, shiny and stiff. After hot curling, a tress treated with Example 12 took a very good curl with fair combability and the hair was left brown, slightly shiny and stiff.

The Curl Drop for each Example was tested under two different humidity conditions and time periods. The first test was run overnight at 25° C. and 50% relative humidity. The average initial length for two tresses treated with Example 11 and hot curled was 6 9/16" and the average Curl Drop after overnight storage at 50% relative humidity was 17/16" (length of tress increased to 7 10/16"). The same procedure was used for Example 12 and the average initial length was 6 9/16", but one tress dropped only 8/16" while the other dropped 19/16" after overnight storage. The same tresses were then placed in a humidity chamber at 25° C. and 65% relative humidity for an additional hour and the average cumulative Curl Drop was found to be 2" 3/16" for Example 11 and the Curl Drop for each tress treated with Example 12 was 1 12/16" and 2 7/16", respectively. On average, both compositions had similar performance in Curl Drop.

EXAMPLE 13-16

These Examples illustrate the use of U.C. MLX 2584 in compositions of the present invention versus a very high molecular weight linear polyethylene oxide polymer (U.C. POLYOX WSR N-3000, 616,000 average molecular weight), U.C. POLYOX WSR N-10 (88,000 average molecular weight) and water. Examples 15 and 16 are comparative examples. The formulations used were as follows:

| Example No. | 13 | 14 | 15 | 16 |
|---|---|---|---|---|
| U.C. MLX 2584 | 1.0 | — | — | — |
| U.C. POLYOX WSR N-10 | — | 1.0 | — | — |
| U.C. POLYOX WSR N-3000 | — | — | 1.0 | — |
| H₂O | 99.0 | 99.0 | 99.0 | 100.0 |

In these Examples, tresses treated with the compositions of Examples 14-15 and the control Example 16 were air dried at 60% relative humidity and room temperature. Example 14 was rated as Stiff— to the touch while Example 15 was rated Stiff and Example 16 was simply Full and not Stiff to the touch. All three Examples resulted in tresses which possessed static upon combing. The tresses for Example 13 were not rated for stiffness after air drying.

Upon hot curling, Example 13 was rated as Stiff— while Examples 14-15 were rated Stiff and Example 16 was Firm, but not Stiff. The Curl Drop observed is reported below (Example 13 was recurled, but was not rewet):

| | Curl Drop, 60% R.H. | | | | |
|---|---|---|---|---|---|
| Example No. | Initial Length | 1 Hour | 4 Hours | (1) | (2) |
| 13 | 6 15/16" | 5/16" | 7/16" | 7 14/16" | 31 |
| 14 | 6 9/16" | 3/16" | 4/16" | 7 13/16" | 39 |
| 15 | 7 2/16" | 9/16" | 14/16" | 8 9/16" | 37 |
| 16 | 7 0/16" | 15/16" | 22/16" | 8 9/16" | 38 |

1 Each tress was combed and allowed to age 1 week at room temperature and ambient relative humidity.
2 Curl diameter in millimeters.

Based on the above results, it is apparent that Example 13 retains the tightest curl with aging based upon Curl Diameter results. Examples 13 and 14 were similar in Curl Drop, but Example 13 gave a tighter curl diameter on aging and the hair tress was not as Stiff as were the tresses treated with Example 14. Examples 15 and 16 were inferior to Example 13 in both Curl Drop and Curl Diameter on aging.

I claim:

1. A method of treating dry hair comprising applying a source of heat in a styling manner to said hair previously treated with a heat activated composition comprising from about 0.1% to about 20% by weight of a water soluble polyethylene oxide polymer in a cosmetically acceptable solvent wherein the polymer is selected from the group consisting of (I) a linear polyethylene oxide polymer consisting of ethyleneoxy units, optionally further containing propyleneoxy units, having an average molecular weight of from about 50,000 to about 250,000 and (II) a branched or cross-linked polymer which is the reaction product of an initiator selected from the group consisting of a polyhydric organic compound having at least three reactive hydrogens selected from the group consisting of alcoholic hydrogens and amine hydrogens, per molecule of said compound, ammonia and an organic epoxide having at least two epoxide groups per molecule with a reactant selected from the group consisting of ethylene oxide, propylene oxide, polyethylene oxide polymers, polypropylene oxide polymers and copolymers of ethylene oxide and propylene oxide and having an average molecular weight in the range of from at least 20,000 to about 250,000, wherein there are no more than about 40 percent propylenoxy units present in said polymer based upon the total moles of ethylenoxy units and propylenoxy units present in said polymer, said polymer being a solid at 25° C. and having a melting point in the range of about 50° to 80° C. and forming a strong, moisture resistant film upon cooling, said heat being sufficient to melt said polyethylene oxide polymer, and removing the source of heat while retaining the hair as it was styled until the polymer has cooled to form said film, thereby styling the hair.

2. The method of claim 1 wherein said polyethyleneoxide polymer is present in an amount of about 0.1 to 6% by weight of the composition.

3. The method of claim 1 wherein the polyhydric compound is selected from the group consisting of glycerol, erythritol, pentaerythritol, sorbitol, diethyleneamine and mixtures thereof.

4. The method of claim 1 wherein the organic epoxide is erythritol anhydride.

5. The method of claim 1 wherein said composition has a pH in the range of about 3-9.

6. The method of claim 1 further including at least one surfactant selected from the group consisting of quaternary ammonium surfactants, 3° amine salts, nonionic emulsifiers, amphoteric surfactants and mixtures thereof, present in an amount up to about 50% by weight of the polymer.

7. The method of claim 1 wherein said polyethylene oxide polymer is the branched or cross-linked polymer of (II) and has an average molecular weight in the range of about 20,000 to 100,000.

8. The method of claim 1 further including a cosmetically acceptable thickening agent present in an amount of about 0.5% to 3% by weight of the composition.

9. The method of claim 1 wherein said solvent is selected from the group consisting of water, ethanol and mixtures thereof.

10. The method of claim 1 wherein said polyethylene oxide polymer is linear polyethylene oxide polymer and has an average molecular weight in the range of about 50,000 to 150,000.

* * * * *